United States Patent [19]

Odessey et al.

[11] Patent Number: 5,100,676
[45] Date of Patent: Mar. 31, 1992

[54] COOL STORAGE OF CULTURED EPITHELIAL SHEETS

[75] Inventors: Richard Odessey, Newton Lower Falls; Alexander Schermer, Belmont; Susan F. Schaeffer, Wayland; Ross A. Tubo, Quincy, all of Mass.

[73] Assignee: Biosurface Technology, Inc., Cambridge, Mass.

[21] Appl. No.: 473,899

[22] Filed: Feb. 2, 1990

[51] Int. Cl.$^5$ ......................... A61K 35/36; C12N 5/00
[52] U.S. Cl. .................................. 424/574; 435/240.2
[58] Field of Search ....................... 435/240.2; 623/15; 424/574

[56] References Cited

U.S. PATENT DOCUMENTS

| | | | |
|---|---|---|---|
| 3,607,646 | 4/1969 | Roissart | 195/1.7 |
| 3,677,024 | 7/1972 | Segall | 62/64 |
| 3,753,357 | 8/1973 | Schwartz | 62/64 |
| 3,772,153 | 11/1973 | Roissart | 195/127 |
| 3,943,993 | 3/1976 | Smith | 165/2 |
| 4,016,036 | 4/1977 | Green et al. | 195/1.8 |
| 4,107,937 | 8/1978 | Chmiel | 62/64 |
| 4,117,881 | 10/1978 | Williams et al. | 165/2 |
| 4,304,866 | 12/1981 | Green et al. | 435/240 |
| 4,423,600 | 1/1984 | McKenna | 62/62 |
| 4,456,687 | 6/1984 | Green | 435/241 |
| 4,559,298 | 12/1985 | Fahy | 435/1 |
| 4,630,448 | 12/1986 | Bilstad et al. | 62/60 |
| 4,681,839 | 7/1987 | Swartz | 435/1 |
| 4,688,387 | 8/1987 | Conaway | 62/78 |
| 4,695,536 | 9/1987 | Lindstrom et al. | 435/1 |
| 4,799,361 | 1/1989 | Linner | 62/64 |

FOREIGN PATENT DOCUMENTS 0296475 6/1988 European Pat. Off. .

OTHER PUBLICATIONS

Biosurface Technology "Cultured Autograft Service Orientation Manual" Mar. 1988.
De Luca et al., Human Epidermis Culture for the Treatment of Burned Patients: A Multicenter Italian Experience, Abstract from Symposium cultured Epithelium, University Hospital, Leiden, The Netherlands; Mar. 28, 1987.
Biosurface Technology "From the Scientists", On the Surface, vol. 1, No. 1, p. 2, Mar., 1989.
Green, Howard, "Terminal Differentiation of Cultured Human Epidermal Cells", Cell, vol. 11, 405–416 (Jun. 1977).
Rheinwald et al., "Defective Terminal Differentiation in Culture as a Consistent and Selectable Character of Malignant Human Keratinocytes", Cell, vol. 22, 626–632 (Nov. 1980).
Pittelkow et al., "Two Functionally Distinct Classes of Growth Arrest States in Human Prokeratinocytes that Regulate Clonogenic Potential", The Journal of Investigative Dermatology, vol. 86, 410–417 (Apr. 1986).
Rosenquist, Marilyn D., "Short-Term Skin Preservation at 4° C.: Skin Storage Configuration and Tissue-to-Volume Medium Ratio", JBCR, vol. 9, 52–54 (Jan./Feb. 1988).
"Epithelial Cell Culturing Service", Biosurface Technology, Inc., Mar., 1988.

Primary Examiner—John Doll
Assistant Examiner—George C. Elliott
Attorney, Agent, or Firm—Testa, Hurwitz & Thibeault

[57] ABSTRACT

The viability of cohesive sheets of cultured epithelial cells such as keratinocytes used as wound dressings is maintained or improved by storage at a temperature within the range of 8°–25° C., preferably 13°–23° C., for periods greater than 8 hours, preferably up to 26 hours. This method and the resulting product permits a significant increase in the shipping radius of cultured dressings manufactured in a central facility, and increases flexibility in scheduling of shipments and surgical procedures.

17 Claims, 5 Drawing Sheets

COOL STORAGE OF CULTURED EPITHELIAL SHEETS

BACKGROUND OF THE INVENTION

This invention relates to short-term storage of cultured tissue. More particularly, the invention relates to short-term storage of cultured epithelial tissue sheets useful as skin wound dressings in a manner which maintains cell viability and colony-forming efficiency.

It has been a priority in the medical community to develop a skin wound dressing which will encourage new growth while preventing fluid loss and infection following skin wounds from burns, ulceration, or surgical excision. Bandages and dressings fail to protect large-scale wounds adequately, and various alternatives have been developed. Among these are split- and full-thickness grafts of cadaver skin, porcine skin, and human allografts and autografts. Most have proved unsatisfactory for covering large wounds since all but autografts eventually are rejected by the body in the absence of immunosuppressive therapy. Autografts are useful in small areas, but for massive injury, conventional autografting is not practical.

Green et al. have developed a method of culturing epithelial cell sheets several cells thick for repairing burns, ulcerations and other skin wounds. U.S. Pat. No. 4,016,036 discloses the method for serially culturing keratinocytes to produce stratified sheets of epithelium. U.S. Pat. No. 4,304,866 discloses the method of producing transplantable cell sheets by culturing keratinocytes and detaching the sheet from its anchorage substratum using an enzyme such as dispase U.S. Pat. No. 4,456,687 discloses agents useful to promote growth of epithelial cells. The disclosure of these patents are incorporated herein by reference. In the culture system developed by Green et al., epithelial cells divide rapidly on the surface of tissue culture dishes or flasks, and ultimately form a confluent, modestly stratified sheet of tightly interconnected cells. These confluent cultures can be released as a cohesive cell sheet by treatment, for example. with the enzyme dispase (see U.S. Pat. No. 4,304,866). The cultured sheets then may be stapled to petrolatum impregnated gauze, or other non-adhesive backing, transported in culture medium to the operating room, and applied to the patient.

Autograft materials prepared by these methods are preferred for burn dressings, but require time to culture. While the autografts are being cultured, it is possible to maintain the wound with allograft material which is effective as a temporary wound dressing. Cultured epidermal allograft material promotes healing of chronic skin ulcers and split-thickness graft donor sites. Cultured epidermal autograft and allograft material made by the method of Green, et al. are now available from Biosurface Technology, Inc. of Cambridge, Mass. for commercial use and clinical trials.

A severe, very practical limitation on the use of cultured epithelial grafts is their limited shelf life. The viability and colony-forming efficiency of the cells in the sheets fall rapidly after they are removed from the anchorage substratum. The cell sheets are extraordinarily fragile. They are reproducibly able to resume growth and form a differentiated epithelium when applied to wounds for a maximum of about eight hours after dispase treatment. This limits the locations to which grafts can be shipped to those in proximity to a production facility. Expanding the availability requires either many production facilities throughout the world, or development of a method of lengthening the viability interval for the cultured sheets.

The art is replete with descriptions of various tissue preservation methods including cryopreservation, use of special cell media, and certain packaging techniques. Cryopreservation allows for long-term storage by freezing the material in the presence of a cryoprotective agent. This agent displaces the aqueous material in the cells and thereby prevents ice crystals from forming. Numerous disclosed protocols vary the nature or amount of cryoprotective agent, and/or the time course, or temperature of the freezing process in an attempt to retain cell viability after a freeze-thaw cycle. See, for example, U.S. Pat. No. 4,559,298, U.S. Pat. No. 4,688,387, and especially EP 0 296 475.

A second method of potentially lengthening the viable storage interval involves selection of the medium which surrounds the cells. For example, U.S. Pat. No. 4,681,839 discloses a system for preserving living tissue separated from its host organism by placing the tissue in a gas-permeable bag containing a "biscuit" which releases electrolytes, a buffering agent, a chemical energy source, high-energy phosphate compounds, metabolites, and sorptive material to remove toxic debris. Also, the patents of DeRoissart describe a method and apparatus for preserving living tissue in a nutrient fluid pressurized with a biochemically inert gas. See U.S. Pat. Nos. 3,607,646 and 3,772,153.

A third method of potentially maintaining viability involves the use of various types of containers such as the corneal storage system described in the Lindstrom et al U.S. Pat. No. 4,695,536, or the container for storing solid living tissue portions of U.S. Pat. No. 4,630,448.

Tissues stored at non-cryopreservation temperatures are commonly stored at 4° C. See Rosenquist et al., "Short-Term Skin Preservation at 4° C.: Skin Storage Configuration and Tissue-to-Volume Medium Ratio" 9(1) J.B.C.R. 52-54 (1988).

Storing tissue by means of cryopreservation is a complicated and expensive process. It is not currently a practical approach for transporting grafts from a production facility to an operating room. None of the other systems has been shown to extend the storage viability beyond very short periods, i.e., eight hours. See, for example, Pittelkow et al., 86 *J. Invest. Dermatol.* 4: 410–17, 413–14 (1986).

This invention seeks to provide a means for extending cultured epithelial graft viability, and to allow extension of the storage and transport time from production facility to the operating room so that life-saving graft materials may be transported long distances while maintaining and/or improving their ability to resume growth and serve as a living epithelial wound covering. The invention also seeks to accomplish these objectives while avoiding shipping the grafts in costly cryopreservation chambers.

SUMMARY OF THE INVENTION

A simple method has now been discovered for maintaining and often improving the colony-forming efficiency of a cultured epithelial sheet following separation from its substrate. This method comprises the step of maintaining the sheet in a sterile environment for a time period in excess of 8 hours at a temperature within the range of about 8° C. to about 25° C., preferably 13° C. to 23° C. Use of this method permits maintenance of the sheet for time periods well in excess of 8 hours, reproducibly for at least as long as 26 hours, and sometimes up to 72 hours, and allows the sheets to be transported easily throughout the world without expensive and complicated cyropreservative packages. This method not only lengthens the viable storage interval of the cultured epithelial sheets, but also for at least the first day of storage usually improves the measured colony-forming efficiency of the cells in the sheets. The percent "take" on patients of grafts stored at the proper temperature for 24 hours after separation from its growth substratum and prior to application to the patient is at least as high as and can be higher than that of grafts stored for fewer than 6 hours.

In another aspect the invention provides a wound dressing, e.g., a skin wound dressing, ready for application to a patient comprising a cohesive living sheet of cultured epithelial cells which has been separated from its substratum for a period in excess of eight hours. This wound dressing has a colony-forming efficiency greater than the colony-forming efficiency of the culture when initially separated.

In another aspect, the invention provides a storage-stabilized product for wound repair comprising a cultured cohesive sheet of human epithelial cells mounted on a nonadherent substrate, housed in a sterile package including means for maintaining the temperature of the sheet within the range of about 8° C. to about 25° C. Maintaining the sheet at a temperature within the range of about 13° C. to about 23° C. for a time period in excess of eight hours has the effect not only of lengthening the viable storage interval but also of often increasing the colony forming efficiency of the cells in the sheet following separation from its substratum. The preferred temperature range is between about 13° C. and about 23° C. The sheets can be maintained at this temperature for about 8-72 hours while maintaining or improving colony forming efficiency.

The epithelial cells preferably are keratinocytes. The cohesive sheet preferably is several cells thick consisting of at least germinative and differentiated cells.

Other objects and features of the invention will be apparent from the drawing, description, and claims which follow.

DETAILED DESCRIPTION

Cultured human epithelial cell sheets can regenerate a permanent epidermis for repair of burns or other epidermal defects. As temporary allograft material, the sheets are also a highly effective burn wound dressing and can promote healing of chronic skin ulcers and split-thickness graft donor sites. The sheets are produced using a culture system developed by Rheinwald and Green, wherein epithelial cells divide rapidly on the surface of tissue culture dishes or flasks and ultimately form a confluent, modestly stratified sheet of tightly interconnected cells. Confluent epithelial cultures can be released as cohesive cell sheets by treatment with an enzyme, such as dispase, then stapled to gauze impregnated with Vaseline ®, transported in culture medium to the operating room, and applied to the patient.

A significant limitation in the use of cultured epidermal grafts is their extreme fragility and short shelf life. Previous experiments had indicated that cell viability in the grafts decreased significantly when the grafts had been separated for longer than 8 hours, as measured by the ability of disaggregated cells to resume growth and form colonies when replated under optimal culture conditions. For this reason, distribution of cultured epithelial sheets was limited geographically, i.e., to those hospitals which could be reached within 8 hours from the time dispase was first added to the cultures to initiate detachment at the production facility. Actual time in transit could be only a few hours as time was consumed in preparing the grafts. Operating room scheduling and time of arrival of the grafts had to be coordinated carefully.

A possible explanation for such a short period of viability of detached epithelial cell sheets was provided by the observation that epithelial cells are found to lose the potential for further division and commit to terminal differentiation when, as single cells disaggregated from cultures by trypsin and EDTA treatment, they are temporarily maintained under conditions that prevent them from reattaching to a surface. Green, Terminal Differentiation of Cultured Human Epidermal Cells. Cell 11:405-16 (1977); and Rheinwald and Beckett, Defective terminal differentiation in culture as a consistent and selectable character of malignant human keratinocytes. Cell 22:629-32 (1980).

Figure 3:
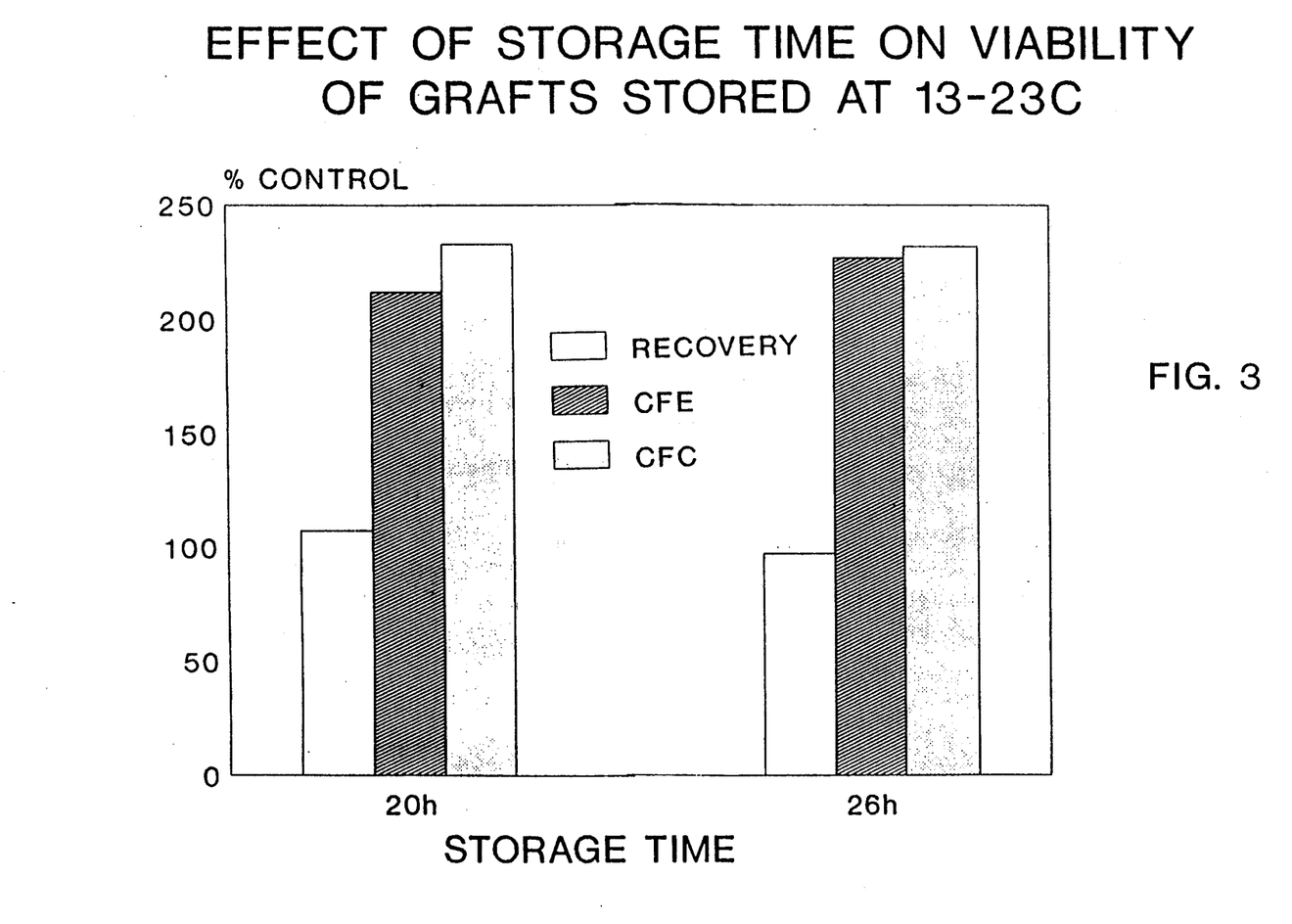
FIG. 3 is a graph displaying the viability of grafts stored at 13°-23° C. for 20 and 26 hrs as a percent of the viability of control grafts, i.e., freshly harvested grafts. The viability is represented as total cell recovery, colony-forming efficiency (CFE) of cells after disaggregation of the cell sheet, and survival of colony forming cells, (CFC). CFC=cells recovered X CFE of the recovered cells.
Figure 4:
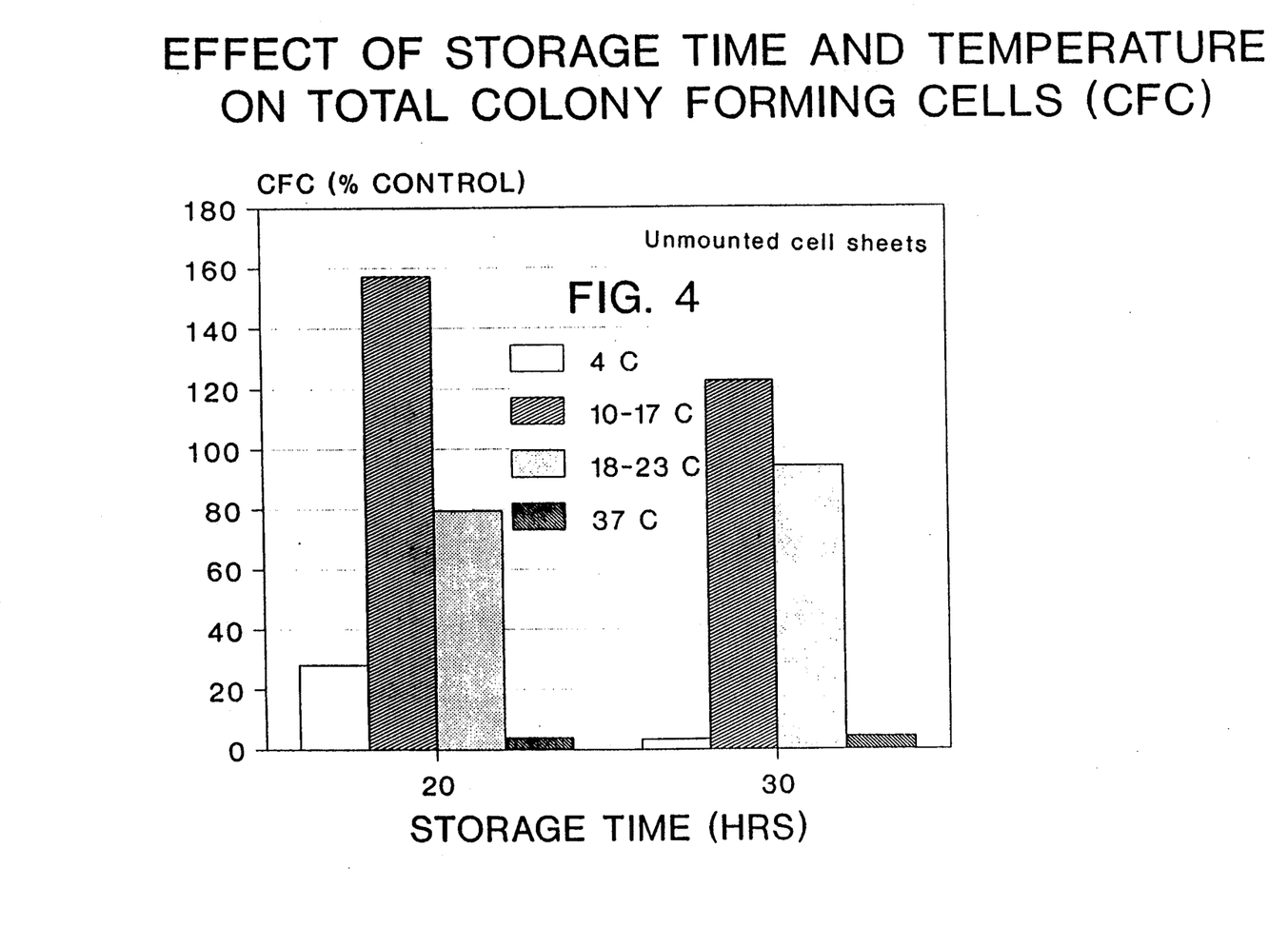
FIG. 4 is a graph summarizing the changes in total colony-forming cells in detached cell sheets stored for 20 to 30 hours at various temperatures.

Experiments assessing viability beyond eight hours revealed that the temperature at which the dispase-treated grafts were maintained was extremely critical to cell viability as measured by colony forming efficiency (CFE) and the total number of colony forming cells recovered (CFC, or total cells recovered X CFE, see FIG. 4). Maintenance of the cultured epithelial sheets at physiological temperature (about 37° C.) failed to maintain the CFC at the level of freshly detached cell sheets. Similarly, maintenance at 4° C. resulted in extensive loss of viability, despite careful control of media conditions, pH, and $CO_2$ balance. However, it was discovered that storing detached epithelial sheets at temperatures within the range of 8° C. to 25° C., preferably 10° C. to 23° C., and more preferably 13° C. to 23° C., maintained or actually increased the viability of the grafts as measured by CFE and CFC (See FIG. 3).

As is evident from the data, attempts to maintain the cell sheets at physiological temperature and at the traditional cold storage temperature for biological samples (4° C.) result in severe decreases in CFC vs. freshly detached sheets. When the sheets are maintained in the preferred temperature range, CFE and CFC actually can improve relative to that of freshly detached sheets. This temperature range is readily maintained by storage with cold packs inside a foam insulated box as described below or by other means.

The results of storage under such conditions may be assessed by controlled experiments designed to measure the graft's suitability as a wound dressing. The ability to generate a well-formed and differentiating epidermis within one week after grafting, as determined by transplanting to the dermis of an athymic (nu/nu) mouse, is useful as an animal model test of graft performance in vivo. By these criteria, the storage period of optimally viable grafts prepared according to the method of the invention is at least 24 hours when the grafts are maintained within a temperature range of 13° C. to 23° C. Other conditions of storage, aside from temperature, may be conventional. It is not critical that the temperature be maintained static during storage, provided the temperature of the graft does not fluctuate significantly outside the range noted above.

The validity of the laboratory studies is supported by the results of four field tests, in which the percent take (the effectiveness of cultured grafts in generating epidermis) of grafts stored for 24 hours before application to the patient was at least as high as that of grafts stored for less than 8 hours. These clinical tests have confirmed that grafts greater than 20 hours old treated in accordance with the invention consistently are at least as effective as 6–8 hour old grafts.

The invention may be understood further in view of the following non-limiting examples.

PREPARATION OF CULTURED EPITHELIAL SHEETS

Cultures were generated by seeding epidermal cells (keratinocytes) into T150 culture flasks at plating densities that reached confluence in 10–12 days. Cultures were maintained in gas-tight flasks at 37° C. in "FAD" medium (a mixture of Dulbecco's modified Eagle's medium (DME) and Hams F12 supplemented with adenine) plus 10% fetal bovine serum (FBS), 0.4 $\mu$g/ml hydrocortisone, 5 $\mu$g/ml insulin, 5 $\mu$g/ml transferrin, $1\times10^{-10}$M cholera toxin, and $2\times10^{-9}$M triiodothyronine) and grown in the presence of lethally irradiated 3T3 fibroblasts. See U.S. Pat. No. 4,016,036. Ten ng/ml epidermal growth factor is included from the first feeding.

The cell cultures were used to prepare grafts within 2 days after reaching confluence. The upper portion of each T150 flask was removed by burning with a soldering iron. The supernatant medium was aspirated and 40 ml of Dispase II (Boehringer Mannheim) at a final concentration of 2.5 mg/ml (approximately 1.2 U/ml) was added to the flask. The lid was replaced and the flask was put into a sterile plastic bag and incubated at 37° C. When the edges of the sheet became detached (−45 min.), the flask was transferred to a laminar flow hood.

The enzyme solution was replaced by 20 ml of DME medium, and the sheet of epithelial cells then was gently dislodged with the aid of a rubber policeman and rinsed again with 20 ml of DME. After aspirating all but 3–4 ml of the second rinse, a $5\times10$ cm piece of petroleum jelly (Vaseline®)-impregnated gauze (Chesebrough Ponds) is placed over each sheet of cells with the superficial cells facing the gauze dressing. The cohesive cell sheet is then attached to the dressings with 12–15 staples (Ligaclips, Ethicon/J&J). The grafts are then transferred to 100 mm dishes with the epithelium facing up. The edges of the graft are pressed to the dish with a rubber policeman to prevent the graft from floating. Twelve ml of DME is gently added and the dish is transferred to the storage container.

Figure 1:
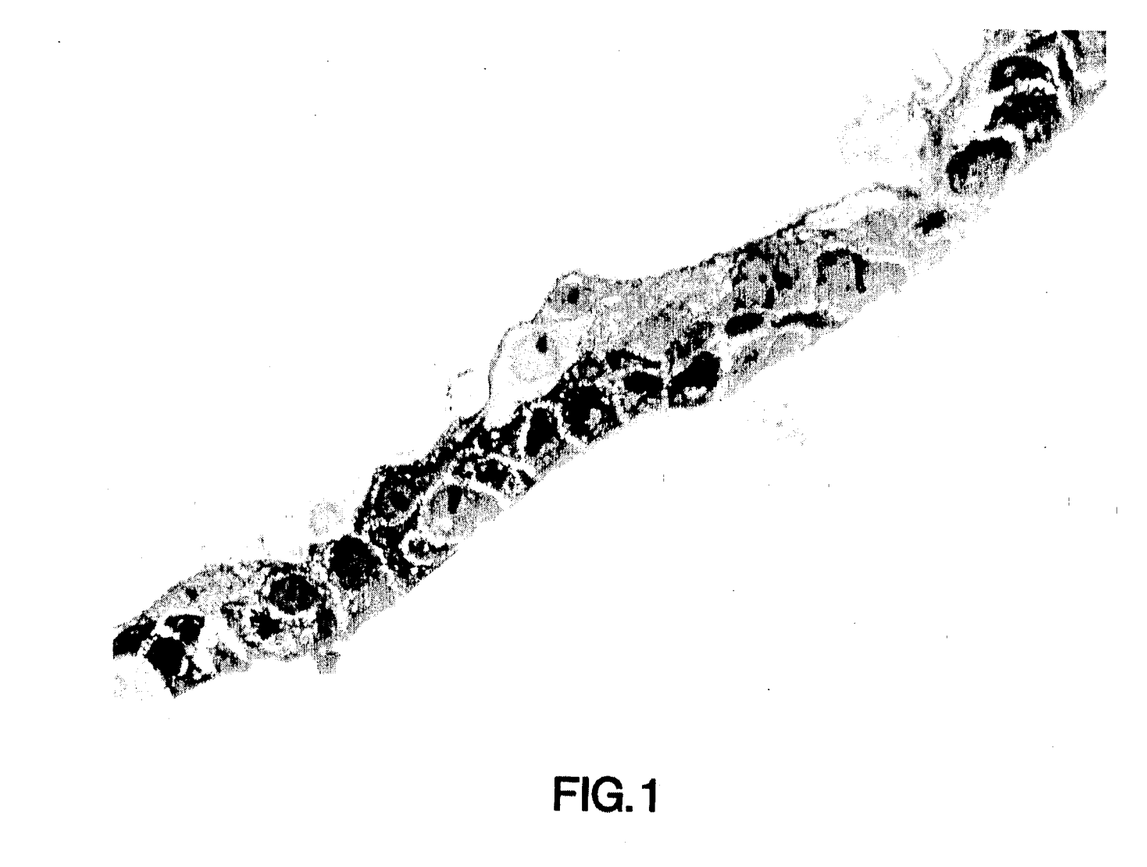
FIG. 1 is a photomicrograph of a perpendicular section of a stratified cultured keratinocyte sheet of the type used in the practice of the invention.

FIG. 1 illustrates a perpendicular section through a typical cultured sheet made in accordance with the foregoing process The cell sheet has been released from the culture dish using Dispase. The basal or germinative layer is the single cell layer nearest the bottom of the photograph. The clear intercellular spaces are a tissue fixation artifact.

TEMPERATURE MAINTENANCE

Figure 2:
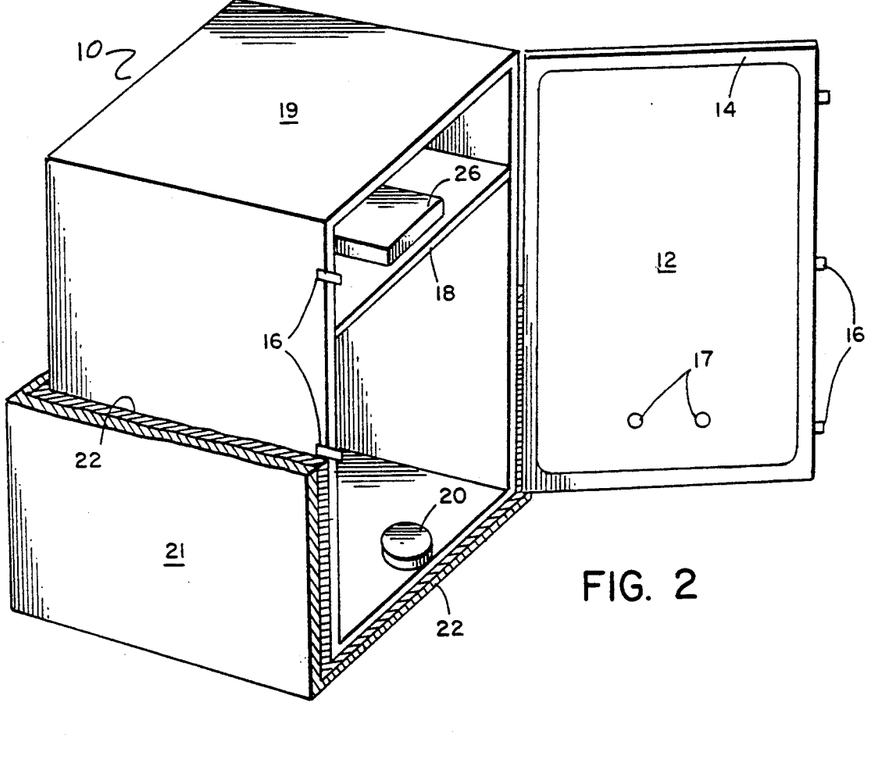
FIG. 2 is an illustration of a container for shipping cultured epithelial sheets suitable for use in the practice of the invention.

Culture dishes containing the grafts may be stored or shipped in a gas-tight box 10 as shown in FIG. 2 constructed of, for example, stainless steel (316L, 16 gauge) with outer dimensions of $11\frac{1}{2}"\times 8\frac{1}{4}"\times 11"$. The door 12 on the box is made from $\frac{1}{4}"$ lexan with a silicon rubber gasket 14 and is sealed with 3 pressure latches 16. Two gas nipples 17 protrude from the door 12. The interior of the box 10 contains a shelf 18 placed near the top 19. The culture dishes 20 containing the grafts are placed in the bottom compartment (up to 63 dishes) and coolant packs 26 are placed on the top shelf 18.

Room temperature storage (21°–23° C.) is achieved simply by placing the box on a lab bench in space maintained within this temperature range. A temperature range of 13° to 23° C. is achieved, for example, by placing on the upper shelf 18, of the chamber 10 two bags 26 each containing 1 Kg of water at 4° C. and one bag 26 containing 250 g of ice at −15° C. A narrower temperature range slightly below ambient may be achieved by placing on the upper shelf four, 12 ounce cold packs (UTEK #412, Polyfoam Packers, Wheeling, IL) previously cooled to 4° C. The steel box is placed within a fiberboard box 21 lined with 1" of styrofoam insulation 22 on all sides.

Figure 5:
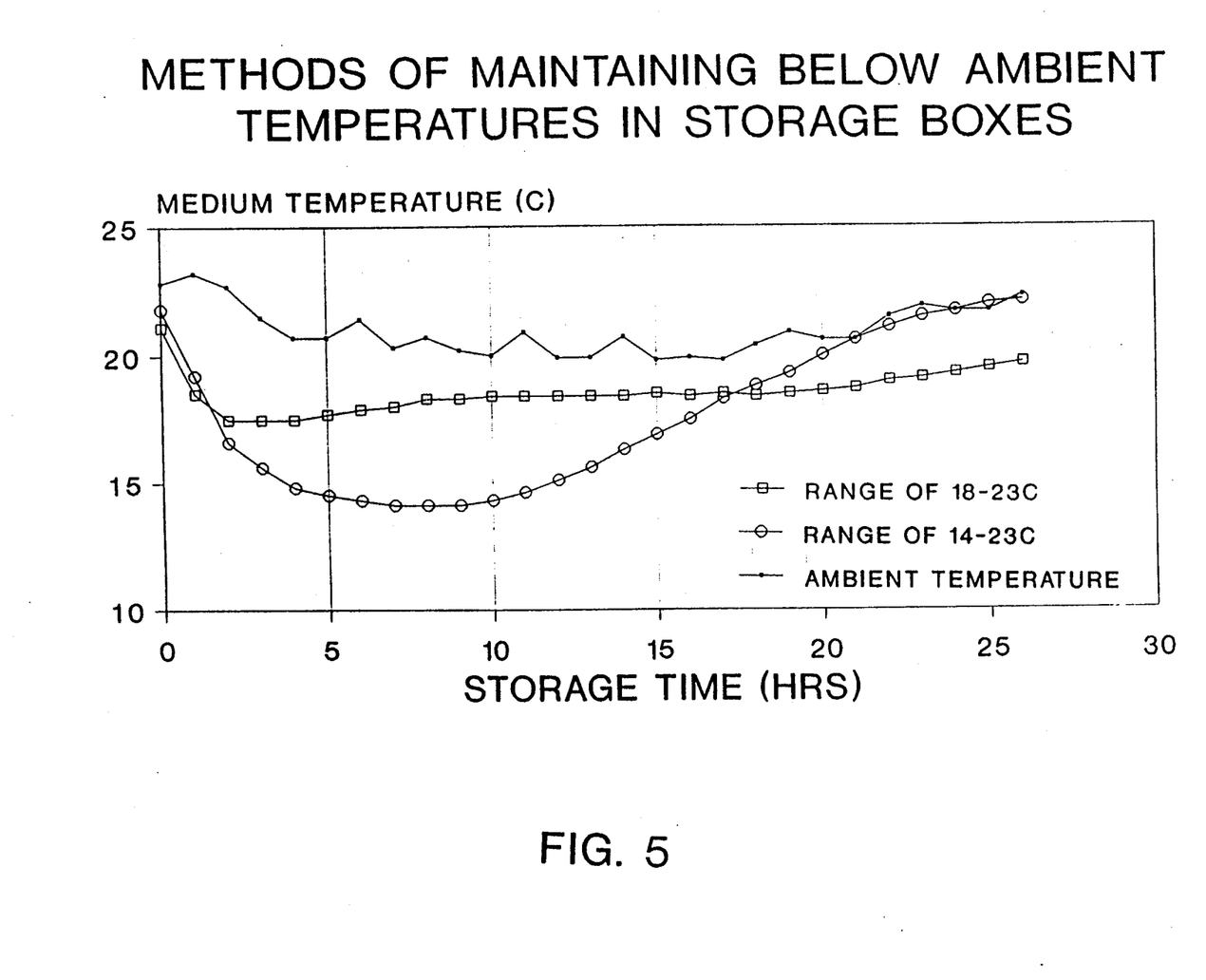
FIG. 5 is a graph of the temperature changes of the graft storage medium in boxes designed as described hereinafter. The temperature was measured with a calibrated electronic thermocouple.

In all cases, the storage chamber is filled with 10% $CO_2$ in air immediately after the grafts are placed inside. Chamber temperature may be monitored with a thermocouple and recorder for experimental purposes. An example of the average temperature profile using the box and cold packs described above is illustrated in FIG. 5. An electronic unit designed to monitor temperature changes adjacent the dishes 20 may be used to indicate to the surgeon whether in shipment the permissible temperature range has been maintained.

EFFICACY OF TEMPERATURE-CONTROLLED STORAGE

Viability assays were performed on grafts that were stored at various temperatures for 20 and 26 hours after detachment from the growth substratum (timed from the addition of dispase), and compared with that of cell sheets within 2 hours after dispase addition (controls). The released cell sheet is dissociated to a single cell suspension in a mixture of trypsin (0.05%) and EDTA (0.01%). Enzymatic action is arrested by addition of calf serum. This is followed by two serial 1:10 dilutions of 0.5 ml cell suspension to 4.5 ml FAD. An aliquot of the initial cell suspension is counted in a hemocytometer and the total number of recovered cells is determined. A final concentration of 2,000 cells/ml is prepared, and 1 ml of this cell suspension is plated into 100 mm dishes in complete medium as described above and maintained at 37° C. in a humidified atmosphere of 10% $CO^2$ in air.

After 14 days, cultures are fixed with 10% formalin in PBS and stained with a mixture of 1% Rhodamine and 1% Nile Blue A. Colonies are counted under a dissecting microscope and scored as either growing or aborted. CFE is calculated as follows:

$$CFE\ \% = \frac{\text{total no. of colonies}}{2000} \times 100$$

The total number of colony forming cells (CFC) is calculated as follows:

CFC = total cell recovery × CFE/100

Five experiments were conducted using three different epithelial cell strains from burn patients who had been candidates for autografting. Cultures were grown and prepared as grafts as described above. Four grafts were used for each time point in each experiment. Grafts were assigned to the different storage times in an experiment such that the two grafts originating from each flask were stored for different times. In addition, an equal number of grafts originating from the front and from the rear of flasks were used for each storage condition. In the 5 experiments conducted during this test, grafts were stored in a foam-insulated box containing prechilled (4° C.) cold packs, as described above.

The total number of cells recovered by trypsin-/EDTA disaggregation from each graft and the colony-forming efficiency of the cells were determined. The total number of colony-forming cells in each graft was then calculated as described above. The results are presented in Table 1 and in FIG. 3. The table shows the results of five experiments in which cultured epithelial grafts attached to gauze backings were stored for up to 26 hours at temperatures between 13° and 23° C. To assay viability, epithelial sheets were enzymatically dissociated into single cells and cell recovery, colony forming efficiency (CFE) and the number of colony forming cells (CFC) per graft were determined at the storage times indicated. The data are summarized further as number of colony forming cells (CFC) remaining relative to that of control grafts.

TABLE 1
SHELF LIFE OF CULTURED EPIDERMAL GRAFTS

| Experiment | 1 | 2 | 3 | 4 | 5 |
|---|---|---|---|---|---|
| Total cells recovered/graft ($\times 10^6$) | | | | | |
| <2.0 hr | 7 | 11.5 | 9.2 | 5.0 | 8.8 |
| 20 hr | 7.4 | 14.0 | 7.3 | 4.4 | 12.5 |
| 26 hr | 5.7 | 14.2 | 6.9 | 3.7 | 11.4 |
| CFE (%) | | | | | |
| <2.0 hr | 2.7 | 1.7 | 3.2 | 3.9 | 6.5 |
| 20 hr | 3.4 | 3.3 | 8.3 | 10.8 | 12.6 |
| 26 hr | 5.5 | 4.5 | 7.7 | 10.0 | 11.1 |
| CFC ($\times 10^6$) | | | | | |
| <2.0 hr | 0.19 | 0.20 | 0.29 | 0.20 | 0.57 |
| 20 hr | 0.25 | 0.46 | .57 | .46 | 1.52 |
| 26 hr | 0.31 | 0.64 | .58 | .37 | 1.17 |
| Relative CFC | | | | | |
| 2 hr | 100% | 100% | 100% | 100% | 100% |
| 20 hr | 182% | 277% | 194% | 224% | 286% |
| 26 hr | 184% | 388% | 196% | 172% | 221% |

Total cells recovered after all times of storage examined was greater than 74% of the control graft (i.e., <2 hours of storage) and averaged 100% over the 5 experiments. There was a very slight, but statistically insignificant, reduction in total cells recovered after 26 hours of storage as compared with 20 hours of storage.

Colony-forming cells recovered were not significantly reduced between 20 and 26 hours of storage, and interestingly, are consistently 2 to 2.5 times as great as that of control grafts. The reason for this unexpected behavior is unknown. However, it is hypothesized that dispase-released and mounted cell sheets may sustain some reversible cell damage. Some of this damage may be spontaneously repaired during the first 20 hours of storage under appropriate temperature conditions, yielding the observed results.

In another series of experiments (see Table 2 below), Strain YF29 (neonatal foreskin) keratinocytes were grown into sheets. In experiment 1, the sheets were released from the plastic using dispase and incubated at 18°-23° C. for the times shown in DME medium in an atmosphere of 10% $CO_2$. In experiments 2 and 3 the sheets were attached to a gauze backing as described above and incubated at the temperatures and times indicated. The results of these experiments indicate substantial survival of CFC at storage times beyond 24 hours. Values ranged from 44%-91% at 44-48 hours and values ranged from 46%-48% at 68-72 hours under the controlled conditions.

TABLE 2
VIABILITY OF EPIDERMAL GRAFTS AFTER PROLONGED STORAGE

| Storage Time (Hrs) | 2-4 | 20-24 | 30 | 44-48 | 55 | 68-72 | 120 |
|---|---|---|---|---|---|---|---|
| EXPERIMENT 1 (18-23° C., Unmounted Cell Sheets) | | | | | | | |
| Total cells recovered/graft ($\times 10^6$) | 4.7 | 4.1 | 3.5 | 2.4 | | 2.6 | |
| CFE (%) | 9.2 | 12 | 8.2 | 8 | | 8 | |
| CFC ($\times 10^6$) | 0.43 | 0.49 | 0.29 | 0.19 | | 0.21 | |
| EXPERIMENT 2 (13-23° C., Mounted on Gauze Backing) | | | | | | | |
| Total cells recovered/graft ($\times 10^6$) | 16 | 12 | | 16.1 | | 8.8 | |
| CFE (%) | 22.9 | 21.1 | | 13.2 | | 19.1 | |
| CFC ($\times 10^6$) | 3.66 | 2.53 | | 2.13 | | 1.68 | |
| EXPERIMENT 3 (17-19° C., Mounted on Gauze Backing) | | | | | | | |
| Total cells recovered/graft ($\times 10^6$) | 19 | 17 | | 19 | 18 | | 15 |
| CFE (%) | 21.3 | 24 | | 19.3 | 19.8 | | 10.1 |
| CFC ($\times 10^6$) | 4.05 | 4.08 | | 3.67 | 3.56 | | 1.52 |
| RELATIVE CFC | | | | | | | |
| EXPERIMENT 1 | 100% | 81% | 77% | 44% | | 48% | |
| EXPERIMENT 2 | 100% | 69% | | 58% | | 46% | |
| EXPERIMENT 3 | 100% | 99% | | 91% | 88% | | 38% |

ANIMAL MODEL FOR ASSESSING GRAFT VIABILITY

Female athymic mice were obtained from Taconic Farm, New York. All mice were of the strain NIH nu/nu and were 6 to 8 weeks old (18-20 g body weight). They were anesthetized by subcutaneous injection of sodium pentobarbital (0.038 mg/g body weight). The mice were kept in a warm cage until they regained consciousness and then were caged separately until grafts were harvested.

Epithelial cell sheets were mounted on Vaseline ® gauze as disclosed above and then stored for 4, 20 and 26 hours in serum-free medium at 18°-22° C. Four grafts were prepared for each storage condition. At grafting, a disc (1 cm in diameter) of sterile Silastic (Dow Corning, N.J.) was inserted between the cell sheet and the gauze backing. Using a sterile scalpel blade, the sheet was cut to the size of the disc. The Silastic disc and adherent epithelium were gently lifted by an edge with forceps and transferred to the site of grafting.

Grafting was carried out according to a variation of the technique of Barrandon, Li, and Green, New Techniques for the Grafting of Cultured Human Epidermal Cells onto Athymic Mice. J. Invest. Dermatol. 91:315-8 (1988). The dorsal surface of the mouse was disinfected with alcohol. A flap was made in the skin with scissors and lifted cranially. The Silastic with the adherent epithelial sheet was gently laid on the thoracic wall just over the rib cage with the basal surface of the epithelium facing upward. The skin flap was folded back in place over the graft and the incision closed with sterile Ligaclips.

To harvest the graft, the animal was sacrificed using ether anesthesia A flap was made which contains the human epithelial graft. The Silastic was peeled away and the mouse tissue surrounding the graft trimmed away. The sample which contains mouse epidermis on its outer surface and human epidermis generated from the graft on its inner surface was then transferred to fixative. Biopsies were fixed in 3.7% formaldehyde and embedded in parrafin. Sections were cut at 5 $\mu$m and stained with Harris' hematoxylin solution in 5% alcoholic eosin. Twelve mice were grafted for the three experimental conditions. The grafts were harvested 7 days after grafting.

The frequency of take was 100%. The human epidermis was visible as a pale area under the mouse skin. When examined after removal of the skin flap, the graft appears as a white area which is clearly demarcated from the surrounding mouse tissue. Differentiation of the keratinocyte sheet into a fully stratified epidermis occurs by 7 days post grafting. In paraffin sections perpendicular to the surface, the four principal layers of human epidermis can be distinguished in the grafts: the stratum basale, stratum spinosum, stratum granulosum and stratum corneum. The stratum basale consists of a single layer of basophilic cells resting on the lamina. Its cells are cuboidal and occasional mitotic figures are observed. The cells of the stratum spinosum have a flattened, polyhedral form. The stratum granulosum consists of two layers of flattened cells whose distinguishing feature is the presence of keratohyaline granules. The thickness of the stratum corneum is variable in the 7 day grafts.

There were no apparent histological differences among grafts stored for 4, 20, and 26 hours. At 7 days, the epidermis is 4-6 cells thick 40 $\mu$m). The 4 layers were present in the same proportion in the three cases. The integrity and order of the stratum basale can be assessed by quantitating the number of nuclei per fixed distance. For all 3 periods of storage, the average number of basal cell nuclei was 9.0 per 100 $\mu$m. Mitotic figures were occasionally observed, but there was no apparent change in their number in different conditions. The most conspicuous feature of the grafts was the prominent nucleated stratum granulosum which, again, is the same in 4, 20, and 26 hour specimens. These results are illustrated in Table 3 below.

TABLE 3

| SHELF LIFE EXPERIMENTS NUDE MICE GRAFTS | | |
|---|---|---|
| Incubation Time (Hr) | Basal Nuclei/ 100 $\mu$m | Thickness of Epithelium ($\mu$m) |
| 4 | 9.0 | 37 |
| 20 | 9.4 | 40 |
| 26 | 9.2 | 37 |

As is apparent from the foregoing, no loss of colony-forming cells or reduction in the ability to form epithelial tissue on a graft bed results from storing cultured epithelial grafts for as long as 26 hours before use, thus demonstrating that the "shelf life" of prepared grafts may be extended from 8 to at least 26 hours. The storage temperature is very important; grafts exhibit optimum retention of colony-forming cells, as measured by the in vitro assay, when stored between 13 and 23° C. Survival of grafts stored at room temperature is nearly as good as slightly lower temperatures.

A temperature range of 15°-20° C. can be maintained easily for about 18 hours (with the chamber temperature subsequently rising to room temperature) if pre-chilled cold packs are placed within the insulated air chamber, and the ambient temperature remains about 21°-23° C. )69.8°-73.4° F.). To maintain an internal box temperature between 13° C. and 23° C. for 24 hours, given an external temperature no lower than about 20° C., and heat stress of the type which may be encountered—air priority shipment, a foam insulated (one inch) box of steel containing 2 liters of 4° C. water in sealed plastic bags and 250 ml of ice will suffice. This type of container may be shipped readily and has a capacity of about 63, 100 mm culture dishes, each containing 12 ml of medium. Of course, other ways to maintain the temperature range effectively, reliably, and inexpensively will occur to those skilled in the art.

The data set forth above indicate that the viability of cultured epithelial graft material can be maintained for at least 26 hours and as long as 72 hours when stored under the described conditions. This conclusion also is supported by the results of five clinical tests which clearly indicate that take of grafts stored for 24 hours before use is at least as high as those applied to the patient within 6 hours of preparation.

The invention may be embodied in other specific forms, and other embodiments fall within the claims which follow.

What is claimed is:

1. A method of improving the colony-forming efficiency in cells of a cultured epithelial cell sheet after separation from its substratum comprising the steps of:
maintaining the sheet in a physiologically compatible medium for a time period greater than 8 hours at a temperature within the range of 8° C. to 19° C.

2. The method of claim 1 wherein the temperature ranges from about 13° C. to about 19° C.

3. The method of claim 1 wherein the time period is 8-26 hours.

4. The method of claim 1 wherein the epithelial cells are keratinocytes.

5. The method of claim 1 wherein the sheet is maintained in an amount of physiologically compatible medium sufficient to submerge said sheet.

6. A dressing suitable for application to a wound comprising a cohesive sheet of cultured, living epithelial cells separated from its anchorage substratum for a period greater than eight hours and characterized by a colony-forming efficiency greater than the colony-forming efficiency of the cells of the cultured confluent sheet when freshly separated from its anchorage substratum.

7. The dressing of claim 6 wherein said cells are keratinocytes.

8. The dressing of claim 6 wherein said cohesive sheet comprises germinative and differentiated cells.

9. A product for wound repair comprising the dressing of claim 6 wherein the cohesive sheet is mounted on a nonadherent substrate and disposed in a package comprising cold packs which absorb heat so that said sheet is maintained within said package at a temperature within the range of 13°-19° C. for at least 12 hours.

10. The product of claim 9 wherein said cells are keratinocytes.

11. The product of claim 9 wherein said cohesive sheet comprises germinative and differentiated cells.

12. A method of lengthening the viable storage interval of a cohesive sheet of living, cultured epithelial cells after separation from its anchorage substratum to maintain said sheet's utility as a skin wound dressing whose cells retain the ability to replicate to form colonies, said method comprising the step of;

maintaining said sheet at a temperature within the range of about 8° C. to 19° C. for a time period exceeding 8 hours.

13. The method of claim 12 wherein the time period is 8-26 hours.

14. The method of treating a wound comprising the steps of:

culturing epithelial cells on an anchorage substratum to form a cohesive sheet;

enzymatically releasing said sheet from the anchorage substratum;

maintaining said sheet for a time period greater than 8 hours at a temperature within the range of 8° C. to 19° C.; and applying said sheet to a wound to permit the cells of said sheet to promote healing of the wound.

15. The method of claim 14 wherein the wound is a skin wound.

16. The method of claim 2 wherein the temperature ranges from about 17° C. to about 19° C.

17. The method of claim 1 wherein the time period is up to about 72 hours.

* * * * *